United States Patent [19]

Clayton et al.

[11] 4,216,223
[45] Aug. 5, 1980

[54] ANTIBACTERIAL COMPOUNDS

[75] Inventors: John P. Clayton, Horsham; Norman H. Rogers, Rudgwick; Steven Coulton, Cranleigh, all of England

[73] Assignee: Beecham Group Limited, United Kingdom

[21] Appl. No.: 962,953

[22] Filed: Nov. 22, 1978

[30] Foreign Application Priority Data

Dec. 3, 1977 [GB] United Kingdom ............... 50443/77

[51] Int. Cl.² ..................... A61K 31/35; C07D 309/06
[52] U.S. Cl. .............................. 424/283; 260/345.7 R; 260/345.8 R; 542/427
[58] Field of Search ................. 260/345.7 R, 345.5 R; 242/427; 424/283

[56] References Cited
U.S. PATENT DOCUMENTS

| 4,102,901 | 7/1978 | Link et al. ...................... 260/345.7 R |
| 4,102,904 | 7/1978 | Link et al. ...................... 260/345.7 R |

FOREIGN PATENT DOCUMENTS 1395907  5/1975  United Kingdom ............. 260/345.8 R Primary Examiner—Nicky Chan
Attorney, Agent, or Firm—Jacobs & Jacobs

[57] ABSTRACT

A thiol acid and esters thereof of formula (II):

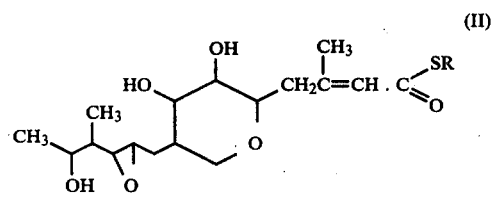

wherein R is hydrogen, a salt forming ion or a pharmaceutically acceptable ester-forming radical, have antibacterial and antimycoplasmal activity and are therefore useful in the treatment of human and veterinary bacterial and mycoplasmal infections.

9 Claims, No Drawings

ANTIBACTERIAL COMPOUNDS

This invention relates to antibacterial compounds and in particular to a thiol acid and esters thereof which have antibacterial activity against certain Gram-positive and Gram-negative organisms, and also possess antimycoplasmal activity. The compounds are therefore of value in the treatment of human and veterinary bacterial and mycoplasmal infections.

Our British cognate patent application No. 24712/76, 40472/76 and 8647/77 discloses an acid of formula (I):

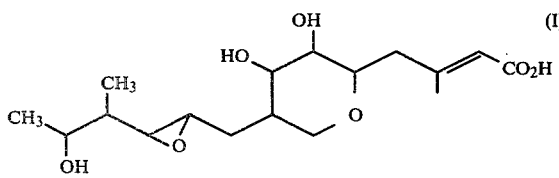

which will be referred to herein as 'monic acid A.' Although this compound does not appear to have antibacterial or antimycoplasmal activity, esters thereof do possess antibacterial and antimycoplasmal activity, as disclosed in our British cognate application No. 23536/77, 23548/77 and 23549/77.

It has now been found that certain thiol esters of monic acid A also possess antibacterial activity and antimycoplasmal activity.

Accordingly the present invention provides a compound of formula (II):

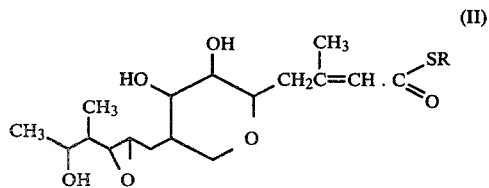

wherein R is hydrogen, a salt-forming ion or a pharmaceutically acceptable ester-forming radical.

The compound (II) of this invention incorporates a trisubstituted double bond and may therefore exist in both the E (natural) and Z (or iso) geometrical forms. It is to be understood that both geometrical isomers of the compound of formula (II) are included within the scope of this invention, as well as mixtures of the two isomers.

When the group R is a salt-forming radical, the salts may be pharmaceutically acceptable, but need not be, as the utility of compound (II) when R is hydrogen or a salt-forming radical is as an intermediate. Suitable salts of the compound include metal salt, e.g. aluminium, alkali metal salts, such as sodium or potassium, alkaline earth metal salts, such as calcium or magnesium, and ammonium or substituted ammonium salts for example those with lower alkylamines such as triethylamine, hydroxy-lower alkylamines such as 2-hydroxyethylamine, bis(2-hydroxyethyl)-amine, or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-α-phenethylamine, dehydroabietylamine, N,N'-bis-dehydroabietylethylenediamine, or bases of the pyridine type such as pyridine, collidine, or quinoline.

Suitable ester-forming radicals for the group R include (a) $C_{1-20}$ alkyl, $C_{2-8}$ alkenyl of $C_{2-8}$ alkynyl each of which may be optionally substituted by $C_{3-7}$ cycloalkyl, halogen, carboxy, $C_{1-6}$ alkoxycarbonyl, carbamoyl, mono- or di-($C_{1-6}$)alkylcarbamoyl, aryl, heterocyclyl, hydroxy, $C_{1-6}$ alkanoyloxy, amino, mono- and di-($C_{1-6}$)alkylamino, $C_{1-6}$ alkanoylamino;

(b) $C_{3-7}$ cycloalkyl optionally substituted with $C_{1-6}$ alkyl;

(c) aryl;

(d) heterocyclyl.

The term "aryl" included phenyl, and naphthyl optionally substituted with up to five halogen, $C_{1-6}$ alkyl, $C_{1-6}$ alkoxy, halo($C_{1-6}$)alkyl, hydroxy, amino, carboxy, $C_{1-6}$ alkoxycarbonyl, or $C_{1-6}$ alkoxycarbonyl ($C_{1-6}$)alkyl groups.

The term "heterocyclyl" includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo($C_{1-6}$)alkyl, hydroxy, amino, carboxy, $C_{1-6}$ alkoxycarbonyl, $C_{1-6}$ alkoxycarbonyl($C_{1-6}$)alkyl, aryl or oxo groups.

Suitable heterocyclyl groups include pyridyl thienyl and furyl.

One suitable substituted alkyl group for the group R has the formula (III):

$$-(CH_2)_n CO_2 R^1 \qquad (III)$$

wherein n is an integer from 1 to 20 and $R^1$ is hydrogen, a pharmaceutically acceptable salt-forming ion or $C_{1-6}$ alkyl.

Thus the group R in compound (II) may be for example $C_{1-6}$ alkyl, in particular, methyl, ethyl n- or iso-propyl, n-, sec-, iso- or tert-butyl; haol-($C_{1-6}$)-alkyl such as trifluoromethyl, 2-chloroethyl, 2,2,2-trichloroethyl; aminoalkyl groups such as aminomethyl, 2-aminoethyl; hydroxymethyl, 2-hydroxyethyl; phenyl; substituted phenyl; a benzyl group; or a group of formula (III) wherein n is an integer from 1 to 8.

One sub-group of compounds of this invention comprises those wherein R is hydrogen, an alkali metal, $C_{1-20}$ alkyl or $C_{2-8}$ alkenyl optionally substituted with phenyl or $C_{1-6}$ alkanoylamino; phenyl, or a group of formula (III) above.

Preferred values for R include $C_{1-6}$ alkyl and $C_{2-6}$ alkenyl.

Other specific examples of the group R include: $C_{7-20}$ alkyl groups such as heptyl, octyl, nonyl, decyl and dodecyl; cyclopropyl, cyclopropylmethyl, cyclopentyl, cyclohexyl, carboxymethyl, methoxycarbonylmethyl, 2-carboxyethyl, 2-methoxycarbonylethyl, 3-methoxycarbonylpropyl, 4-methoxycarbonyl-n-butyl, 5-methoxycarbonyl-n-pentyl, 6-methoxycarbonyl-hexyl, 7-methoxycarbonyl-n-heptyl, 10-methoxycarbonyldecyl, carbamoylmethyl, furylmethyl, benzyl, 2,4,6-trichlorophenyl, pentachlorophenyl, o-, m- or p-methylphenyl, o-, m- or p-methoxycarbonylphenyl, 2- or 3- or 4-pyridyl, prop-2-enyl, prop-2-ynyl, 2-dialkylaminoethyl, or 3-methoxycarbonylprop-2-enyl.

Specific compounds of the present invention include the following esters of monic acid A:

phenylthiol (R=—$C_6H_5$);
ethanethiol (R=—$C_2H_5$);
benzylthiol (R=—$CH_2C_6H_5$);
n-butanethiol (R=n—$C_4H_9$);

methanethiol (R=CH$_3$);
1-methoxycarbonylmethanethiol (R=—CH$_2$CO$_2$CH$_3$);
2-acetamidoethanethiol (R=—CH$_2$CH$_2$NHCOCH$_3$);
prop-2-enethiol (R=—CH$_2$—CH=CH$_2$).

The compounds of the present invention may be prepared by reacting monic acid A of formula (I) above, or a reactive derivative thereof with a thiol of formula RSH or a reactive derivative thereof.

The choice of reactive derivative for monic acid A will depend on whether a reactive derivative of the thiol RSH is employed; and will also be influenced by the nature of the group R.

The reactive derivative of monic acid A may be a symmetrical or mixed anhydride. Suitable mixed anhydrides are alkoxyformic anhydrides, or anhydrides with, for example, alkanoic acids such as trimethyl acetic acid, thioacetic acid, diphenylacetic acid; or with benzoic acid, phosphorus acids (such as phosphoric or phosphorous acids), sulphuric acid or aliphatic or aromatic sulphonic acids (such as p-toluenesulphonic acid). Anhydrides with alkanoic acids such as trimethylacetic acid are suitable when R is an aryl or heterocyclic group (type (c) or (d) above) such as phenyl and the anhydride of monic acid A may be reacted directly with the thiol RSH. Alkanoic acid mixed anhydrides are however less suitable when the group R is of the type (a) or (b) above, especially alkyl or substituted alkyl. In this case other mixed anhydrides, such as with phosphorus acids, may be employed. A preferred manner of preparing compounds (II) when R is an alkyl or substituted alkyl group is reacting the mixed anhydride formed from monic acid A and diethyl phosphorochloridate with a thiolate salt, M$^+$S$^-$R, where M$^+$ is a metal ion such as thallium (I) or an alkali metal such as sodium or potassium.

Other suitable reactive derivatives of monic acid A include an acid halide, preferably the acid chloride or bromide which may be reacted with a salt of the thiol RSH. The acid halide may be prepared by reacting the monic acid or a salt thereof with a halogenating agent such as phosphorus pentachloride, thionyl chloride or oxalyl chloride.

Activated esters of monic acid A may also be employed as reactive derivatives. Examples include esters of N-hydroxysuccinimide, 1-hydroxy-1H-benzotriazole, 3-hydroxy-4-oxo-3,4-dihydro-1,2,3-benzotriazine, pentachlorophenol and the enol ester from 4-dimethylamino-3-butyn-2-one.

Other reactive derivatives of monic acid A include the reactive intermediate formed by reaction in situ with a condensing agent such as a carbodiimide optionally together with 4-dimethylaminopyridine, for example N,N-diethyl-, dipropyl- or diisopropylcarbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-cabonylditriazole; an isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline.
Other condensing agents include Lewis acids (for example BBr$_3$—C$_6$H$_6$); or a phosphoric acid condensing agent such as diethylphosphorylcyanide. The reaction is preferably carried out in an organic reaction medium, for example dichloromethane, dimethylformamide, acetonitrile, alcohol, benzene, dioxan, or tetrahydrofuran.

A preferred condensing agent is dicyclohexylcarbodiimide in the presence of 4-dimethylaminopyridine.

The compound of formula (II) in which R represents hydrogen may also be prepared by the above process. Preferably when R is hydrogen, either monic acid A is reacted with hydrogen sulphide or a mixed anhydrode of the acid is reacted with a thiolate salt, such as sodium thiolate, NaSH.

The compounds of the present invention also may be prepared from the intermediate ketone of formula (IV) by any method known to convert a ketone into an α,β-unsaturated thio-acid or ester. One such process comprises reacting a compound of formula (IV) in which the hydroxyl hydroxyl groups may be protected with a compound of formula (V) or (VI):

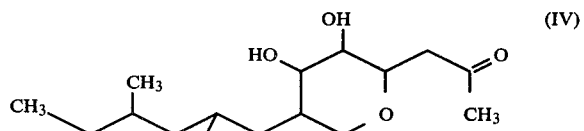

in which formulae (V) and (VI) the symbols R$_a$, R$_b$ and R$_c$ are the same or different and each is lower alkyl, aryl or aralkyl, and R is as defined with respect to formula (II) above; and subsequently removing any hydroxyl protecting groups.

The preferred embodiment of this process comprises reacting compound (IV) with compound (V). Preferably in this case R$_a$ and R$_b$ are methyl or ethyl. In the case when compound (IV) is reacted with compound (VI), then R$_a$, R$_b$ and R$_c$ are preferably all phenyl.

The reaction is usually carried out in an inert solvent such as dimethylformamide, hexane, benzene, tetrahydrofuran for example, at a temperature of from about 10° C. to about 100° C. preferably under an inert gas such as nitrogen. Under these conditions the reaction proceeds smoothly over a period of from a few minutes to a few hours and the product may be isolated by any of the usual techniques e.g. solvent evaporation or anti-solvent precipitation followed by filtration. In many cases the reaction may be carried out in a solvent in which the product is insoluble and in such cases the precipitated solid may be collected by filtration. Purification of the product may be by any of the usual chromatographic or recrystallisation techniques.

Compounds of formula (II) wherein R is an ester-forming radical may also be prepared by esterification of compound (II) wherein R is hydrogen or a salt or other reactive derivative of the acid. Esterification may be performed by any conventional method, for example by reaction of the free acid:
 (a) with the appropriate thiol or alcohol in the presence of a catalyst such as a strong acid, dry hydrogen chloride or p-toluenesulphonic acid; or
 (b) with the appropriate halide or sulphate of the alcohol in the presence of dimethylsulphoxide and calcium carbonate or with the halide in the presence of hexamethyl phosphoramide; or (c) by phase transfer catalysis methods with the halide and/or sulphate of the alcohol in aqueous and/or organic solution in the presence of a quaternary ammonium salt such as tetrabutyl ammonium bisulphate or halide, or benzyltrimethylammonium halide; or (d) with a diazoalkane.

The antibiotic compounds according to the invention may be formulated for administration in any convenient way for use in human or veterinary medicine, by analogy with other antibiotics, and the invention therefore includes within its scope a pharmaceutical composition comprising a compound of formula (II) above together with a pharmaceutical or veterinary carrier or excipient.

The compositions may be formulated for administration by any route, and would depend on the disease being treated. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lypophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration. Where the compositions comprise dosage units, each unit will preferably contain from 50-500 mg., of the active ingredient. The dosage as employed for adult human treatment will preferably range from 100 to 3000 mg, per day, for instance 1500 mg, per day, depending on the route and frequency of administration.

The following Examples illustrate this invention.

EXAMPLE 1

Thiophenyl Monate A

Monic acid (0.344 g; 1 mM) was dissolved in dry tetrahydrofuran (20 ml) and the solution cooled to $-10°$ C. Triethylamine (0.101 g; 140 μl; 1 mM) and isobutylchloroformate (0.137 g; 130 μl; 1 mM) were added and the solution stirred at $-10°$ C. for 15 minutes. Thiophenol (0.110 g; 103 μl; 1 mM) was then added and the solution stirred at $0°$ C. for 30 minutes and room temperature of 2 hours. The solvent was then removed at reduced pressure and the residue partitioned between ethyl acetate and sodium bicarbonate solution. The organic layer was washed with saturated brine and dried over anhydrous magnesium sulphate. Removal of the solvent at reduced pressure afforded a colourless oil, which was purified by column chromatography over silica gel (12 g; Type 60). Elution with 5% methanol/chloroform yielded the pure (hplc and tlc) thiophenyl monate as an oil, which on trituration with dry diethyl ether gave a white solid (0.200 g; 46%). M.pt. $118°$-$119°$ C. (Found: C, 63.12; H, 7.39; S, 7.36. $C_{23}H_{32}O_6S$ requires: C, 63.28; H, 7.39; S, 7.34%). $[\alpha]_D^{20} = -41.7°$ (c 1.0, $CHCl_3$), $\lambda_{max}$ (EtOH) 240 nm ($\epsilon_m$ 19,400), 264 ($\epsilon_m$ 10,400), $\nu_{max}$ ($CHBr_3$) 3400, 1685 and 1620 $cm^{-1}$ $\delta_H$ ($CDCl_3$) 7.33 (5H, s, aromatic protons), 6.10 (1H, s, C$\underline{H}$=C),

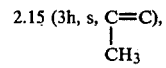

2.15 (3h, s, C=C),
       |
       CH₃

1.20 (3H, d, J=6.5 Hz, C$\underline{H}_3$—14), 0.91 (3H, d, J=7.0 Hz, C$\underline{H}_3$—17), $\delta_C$ ($CD_3OD$) 188.8 (s), 158.0 (s), 135.7 (d), 130.1 (d), 129.8 (s), 124.3 (d), 116.8 (d), 76.2 (d), 71.6 (d), 69.9 (d) 66.4 (t), 61.3 (d), 56.9 (d), 43.7, 41.6 (d), 32.9 (t), 20.4 (q), 12.3 (q).

EXAMPLE 2

Thioethyl Monate A

To a solution of monic acid (0.344 g; 1 mM) and triethylamine (0.101 g; 140 μl; 1 mM) in dry tetrahydrofuran (10 ml) was added a solution of diethyl phosphorochloridate (0.173 g; 1 mM) in dry tetrahydrofuran (5 ml), at room temperature under an argon atmosphere. The mixture was stirred at room temperature for 3 hours, and the precipitated triethylamine hydrochloride was removed by filtration. The solid was washed with tetrahydrofuran and to the combined filtrate and washings was added thallium (I) ethanethiolate (0.265 g; 1 mM). The resulting suspension was stirred at room temperature for three days and then filtered through a celite plug. The solvent was removed at reduced pressure and the residue partitioned between ethyl acetate and sodium bicarbonate solution. The organic layer was washed with saturated brine and dried over anhydrous magnesium sulphate. Removal of the solvent at reduced pressure gave the crude thiol ester as a colourless oil (0.380 g). This oil was purified by column chromatography over silica gel (Type 60; 10 g). Elution with 5% methanol/chloroform afforded the pure (by hplc and tlc) thoiethyl monate as a colourless oil. Trituration with dry diethyl ether gave a white solid (0.205 g; 53%). M.pt. 80°–81° C. (Found: C, 59.03; H, 8.24; S, 8.38. $C_{19}H_{32}SO_6$ requires: C, 58.74; H, 8.30; S, 8.25%). $[\alpha]_D^{20} -8.3°$, (c 1.0, $CHCl_3$), $\lambda_{max}$ (EtOH) 237 nm ($\epsilon_m$ 9,682), 268 nm ($\epsilon_m$ 8,150), $\nu_{max}$ (nujol) 3425, 1680 and 1620 cm$^{-1}$, $\delta_H$ (CDCl$_3$) 6.0 (1H, s, C$\underline{H}$=C);

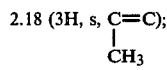

2.18 (3H, s, C=C);
|
CH$_3$ 1.25 (6H, t, C$\underline{H}_3$—14 and SC$\underline{H}_2$CH$_3$); 0.92 (3H, d, J=7.0 Hz, C$\underline{H}_3$—17), $\delta_C$ (CDCl$_3$) 189.6, 153.6, 124.7, 74.9, 71.3, 70.3, 68.9, 65.4, 61.3, 55.6, 42.8, 42.6, 39.5, 31.6, 23.2, 20.8, 20.0, 14.8 and 12.7, m/e 227 (5%), 111 (50%), 62 (100%), No M$^+$.

EXAMPLE 3

Thiobenzyl Monate A

To a solution of monic acid (1.032 g; 3 mM) and triethylamine (0.303 g; 420 μl; 3 mM) in dry tetrahydrofuran (30 ml) was added a solution of diethyl phosphorochloridate (0.518 g; 3 mM) in dry tetrahydrofuran (10 ml), at room temperature under an argon atmosphere. The solution was stirred at room temperature for three hours and the precipitated triethylamine hydrochloride was removed by filtration. To the filtrate was added thallium (I) benzylthiolate (0.981 g; 3 mM). The resulting suspension was stirred at room temperature for 16 hours and then filtered through a celite plug. The solvent was removed at reduced pressure and the residue partitioned between ethyl acetate and sodium bicarbonate solution. The organic layer was washed with saturated brine and dried over anhydrous magnesium sulphate. Removal of the solvent at reduced pressure gave the crude thiol ester as a colourless oil (1.0 g). This oil was purified by column chromatography over silica gel (Type 60; 25 g). Elution with 5% methanol/chloroform afforded the pure (by hplc and tlc) thiobenzyl monate as a colourless oil (0.730 g; 54%). $\mu_{max}$ (EtOH) 235 nm ($\epsilon_m$ 10, 950), 270 nm ($\epsilon_m$ 8,300), $\nu_{max}$ (CHBr$_3$) 3400, 1670 and 1620 cm$^{-1}$, $\delta_H$ (CDCl$_3$) 7.18 (5H, m, aromatic H); 5.98 (1H, s, C$\underline{H}$=C); 4.07 (2H, s, SC$\underline{H}_2$); 2.18 (3H, s, C$\underline{H}_3$—15); 1.17 (3H, d, J=6.0 Hz, C$\underline{H}_3$—14); 0.88 (3H, d, J=6.0 Hz, C$\underline{H}_3$—17), $\delta_C$ (CDCl$_3$) 188.1, 154.7, 137.7, 129.0, 128.5, 128.2, 126.7, 123.6, 74.6, 70.4, 69.9, 68.5, 65.1, 60.6, 55.2, 42.3, 39.4, 32.7, 31.3, 20.2, 19.9, 12.1, m/e 327.1808 ($C_{17}H_{27}O_6$ requires 327.1808; 0.2%), 281 (2%), 263 (25%), 246 (6%), 235 (13%), 132 (10%), 131 (20%), 91 (100%), No M$^+$. $[\alpha]_D^{20} -6.11°$ (c 1.0, CHCl$_3$).

EXAMPLE 4 n-Butanethiol Ester of Monic Acid A

To a solution of monic acid (1.032 g; 3 mM) and triethylamine (0.30 g; 420 μl; 3 mM) in dry tetrahydrofuran (30 ml) was added a solution of diethyl phosphorochloridate (0.518 g; 3 mM) in dry tetrahydrofuran (10 ml), at room temperature under an argon atmosphere. The mixture was stirred at room temperature for three hours, and the precipitated triethylamine hydrochloride was removed by filtration. To the filtrate was added thallium (I) n-butanethiolate (0.879 g; 3 mM). The resulting suspension was stirred at room temperature for 16 hours and then filtered through a celite plug. The solvent was removed at reduced pressure and the residue partitioned between ethyl acetate and sodium bicarbonate solution. The organic layer was washed with saturated brine and dried over anhydrous magnesium sulphate. Removal of the solvent at reduced pressure gave the crude thiol ester as a colourless oil (1.10 g). This oil was purified by column chromatography over silica gel (Type 60; 15 g). Elution with 5% methanol/chloroform afforded the pure (by hplc and tlc) n-butanethiol ester of monic acid as a colourless oil (0.957 g; 77%). $\lambda_{max}$ (EtOH) 238 nm ($\epsilon_m$ 10,600), 270 nm ($\epsilon_m$ 8,770), $\nu_{max}$ (CHBr$_3$) 3420, 1670 and 1620 cm$^{-1}$, $\delta_H$ (CDCl$_3$) 6.0 (1H, s, C$\underline{H}$=C);

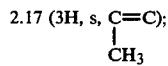

2.17 (3H, s, C=C);
|
CH$_3$ 1.19 (3H, d, J=6.5 Hz, C$\underline{H}_3$—14); 0.91 (6H, d+t, C$\underline{H}_3$—17 and alkyl C$\underline{H}_3$), $\delta_C$ (CDCl$_3$) 189.3, 153.5, 124.3, 74.7, 70.5, 70.0, 68.6, 65.0, 60.7, 55.3, 42.4, 39.3, 31.4, 28.2, 21.7, 20.3, 19.7, 13.3, and 12.2. m/e 327.1806 ($C_{17}H_{27}O_6$ requires 327.1808; 3%), 300 (4%), 227 (12%), 111 (30%), 101 (100%). No M$^+$. $[\alpha]_D^{20} -7.15°$ (c 1.0, CHCl$_3$).

EXAMPLE 5

Methanethiol Ester of Monic Acid A

To a solution of monic acid (2.064 g; 6 mM) and triethylamine (0.840 ml; 6 mM) in dry tetrahydrofuran (50 ml) was added diethyl phosphorochloridate (1.035 g; 6 mM), at room temperature under an argon atmosphere. The mixture was stirred at room temperature for three hours and the precipitated triethylamine hydrochloride was removed by filtration. The solid was washed with tetrahydrofuran and to the combined filtrate and washings was added thallium (I) methanethiolate (1.506 g; 6 mM). The resulting suspension was stirred at room temperature for sixteen hours and then filtered through a celite plug. The solvent was removed at reduced pressure and the residue partitioned between ethyl acetate and sodium bicarbonate solution. The organic layer was washed with saturated brine and dried over anhydrous magnesium sulphate. Removal of the solvent at reduced pressure gave the crude thiol ester as a colourless oil. This oil was purified by column chromatography over silica gel (Type 60; 25 g). Elution with 5% methanol/chloroform afforded the pure methanethiol ester of monic acid A as a colourless oil, which crystallised with ether (1.10 g; 49%). M.pt. 74°–75° C. (ether). (Found: C, 58.0; H, 8.1; S, 8.8 $C_{18}H_{30}SO_6$ requires: C, 57.7; H, 8.1; S, 8.6%), $[\alpha]_D^{20} -9.25°$ (c 1.0 CHCl$_3$), $\lambda_{max}$ (EtOH) 237 nm ($\epsilon_m$ 12,100), 268 nm ($\epsilon_m$ 10,300), $\nu_{max}$ (CHBr$_3$) 3440, 1660 and 1620 cm$^{-1}$, $\delta_H$ (CDCl$_3$) 6.01 (1H, s, C$\underline{H}$=C); 2.28 (3H, s, —SCH$_3$); 2.17 (3H, s, CH$_3$—15); 1.20 (3H, d, J=6.5 Hz, C$\underline{H}_3$—14); 0.91 (3H, d, J=6.0 Hz, C$\underline{H}_3$—17), $\delta_c$ (CDCl$_3$) 190.0, 154.0, 124.4, 75.0, 70.9, 70.4, 68.9, 65.4, 61.1, 55.7, 42.7, 39.7, 31.6, 20.6, 20.1, 12.5, 11.5, m/e 327.1812 ($C_{17}H_{27}O_6$ requires 327.1808; 10%), 227 (20%), 169 (10%), 141 (23%), 111 (100%), no M+.

EXAMPLE 6

1-Methoxycarbonylmethanethiol Ester of Monic Acid A

To a solution of monic acid (2.06 g; 6 mM) and triethylamine (0.840 ml; 6 mM) in dry tetrahydrofuran (50 ml) was added diethyl phosphorochloridate (1.035 g; 6 mM), at room temperature under an argon atmosphere. The mixture was stirred at room temperature for three hours and the precipitated triethylamine hydrochloride was removed by filtration. The solid was washed with tetrahydrofuran and to the combined filtrate and washings was added sodium 1-methoxycarbonylmethanethiolate (0.768 g; 6 mM). The resulting suspension was stirred at room temperature for 16 hours and then filtered through a celite plug. The solvent was removed at reduced pressure and the residue partitioned between ethyl acetate and sodium bicarbonate solution. The organic layer was washed with saturated brine and dried over anhydrous magnesium sulphate. Removal of the solvent at reduced pressure gave the crude thiol ester as a colourless oil. This oil was purified by column chromatography over silica gel (Type 60; 25 g). Elution with 5% methanol/chloroform afforded the pure 1-methoxycarbonylmethanethiol ester of monic acid A as a colourless oil, (1.029 g; 40%), $[\alpha]_D^{20} -5.71°$ (c, 1.0 CHCl$_3$), $\lambda_{max}$ (EtOH) 242 nm ($\epsilon_m$ 10,400), 265 nm ($\epsilon_m$ 9,750), $\nu_{max}$ (CHBr$_3$) 3400, 1735, 1678 and 1620 cm$^{-1}$, $\delta_H$(CDClhd 3) 6.02 (1H, s, C$\underline{H}$=C); 3.68 (3H, s, CO$_2$CH$_3$); 2.18 (3H, s, CH$_3$—15); 1.19 (3H, s, J=6.0 Hz, CH$_3$—14); 0.92 (3H, d, J=6.0 Hz, CH$_3$—17), $\delta_c$ (CDCl$_3$) 186.9, 170.0, 156.6, 123,4, 75.0, 70.8, 70.4, 68.8, 65.6, 65.4, 61.0, 55.7, 52.7, 42.7, 39.8, 31.7, 206, 20.4, and 12.5.

EXAMPLE 7

2-Acetamidoethanethiol Ester of Monic Acid A

To a solution of monic acid (1.032 g; 3 mM) and triethylamine (0.420 ml; 3 mM) in dry tetrahydrofuran (50 ml) was added diethyl phosphorochloride (0.518 g; 3 mM), at room temperature under an argon atmosphere. The mixture was stirred at room temperature for three hours and precipitated triethylamine hydrochloride was removed by filtration. The solid was washed with tetrahydrofuran and to the combined filtrate and washings was added the sodium salt of N-acetyl-$\beta$-mercaptoethylamine (0.423 g; 3 mM). The resulting suspension was stirred at room temperature for three days and then filtered through a celite plug. The solvent was removed at reduced pressure and the residue partitioned between ethyl acetate and sodium bicarbonate solution. The organic layer was washed with saturated brine and dried over anhydrous magnesium sulphate. Removal of the solvent at reduced pressure gave the crude thiol ester as a pale yellow oil. This oil was purified by column chromatography over silica gel (Type 60; 50 g). Elution with 5% methanol/chloroform afforded the pure 2-acetamidoethanethiol ester of monic acid A as a colourless oil, (0.310 g; 23%). $[\alpha]_D^{20} -7.04°$ (c, 1.0 CHCl$_3$)$\nu_{max}$ (CHBr$_3$) 3350, 1660 and 1625 cm$^{-1}$, $\lambda_{max}$ (EtOH) 240 nm ($\epsilon_m$ 9,630), 267 nm ($\epsilon_m$ 8,390), $\delta_H$(CDCl$_3$) 6.67 (1H, broad resonance, NH); 6.02 (1H, s, C$\underline{H}$=C); 2.17 (3H, s, CH$_3$—15); 1.94 (3H, s, COC$\underline{H}_3$); 1.19 (3H, d, J=6.0 Hz, CH$_3$—14); 0.92 (3H, d, J=6.5 Hz, CH$_3$—17), $\delta_c$ (CDCl$_3$), 189.3, 171.0, 155.7, 124.2, 75.0, 71.1, 70.4, 68.9, 65.5, 61.1, 55.7, 42.8, 39.9, 31.7, 28.5, 23.1, 20.8, 20.3, and 12.6. m/e 327.1799 (3% $C_{17}H_{27}O_6$ requires 327.1808).

EXAMPLE 8

Prop-2-enethiol Ester of Monic Acid A

To a solution of monic acid (1.032 g; 3 mM) and triethylamine (0.420 ml; 3 mM) in dry tetrahydrofuran (50 ml) was added diethyl phosphorochloridate (0.518 g; 3 mM), at room temperature under an argon atmosphere. The mixture was stirred at room temperature for 3 hours and the precipitated triethylamine hydrochloride was removed by filtration. The solid was washed with tetrahydrofuran and to the combined filtrate and washings was added thallium (I) 2-propene-1-thiolate (0.830 g: 3 mM). The resulting suspension was stirred at room temperature for 16 hours and then filtered through a celite plug. The solvent was removed at reduced pressure and the residue partitioned between ethyl acetate and sodium bicarbonate solution. The organic layer was washed with saturated brine and dried over anhydrous magnesium sulphate. Removal of the solvent at reduced pressure gave the crude thiol ester as a yellow oil. This oil was purified by column chromatography over silica gel (Type 60; 50 g). Elution with 5% methanol/chloroform afforded the pure prop-2-enethiol ester of monic acid A as a colourless oil, (0.230 g; 19%), $\lambda_{max}$ (EtOH) 239 nm ($\epsilon_m$ 11,220), 269 nm ($\epsilon_m$ 9,700), $\nu_{max}$ (CHBr$_3$) 3425, 1675 and 1620 cm$^{-1}$, $\delta_H$ (CDCl$_3$) 6.00 (1H, s C$\underline{H}$=C); 5.5–5.95 (1H, m, C$\underline{H}$=C); 5.18 (dd, J=16 Hz and 1 Hz); 5.03 (dd, J=9.5 Hz and ca 1 Hz, 2H between 4.9 and 5.3, C=CH$_2$ protons); 2.17 (3H, s, CH$_3$—15); 1.19 (3H, d, J=6.0 Hz, CH$_3$—14); 0.91 (3H, d, J=7.0 Hz, CH$_3$—17), $\delta_c$ (CDCl$_3$) 188.6, 154.4, 133.5, 124.3, 117.6, 75.0, 71.3, 70.3, 68.9, 65.5, 61.3, 55.6, 42.9, 39.6, 31.7, 20.8, 20.2, and 12.7, m/e 327.1798 (14%; $C_{17}H_{27}O_6$ requires 327.1807), no M+.

EXAMPLE 9

Prop-2-enethiol Ester of Monic Acid A

To a stirred solution of monic acid A (2.064 g; 6 mM) in anhydrous dichloromethane (100 ml) was added 4-dimethylaminopyridine (0.075 g; 0.6 mM) and allyl mercaptan (approx. 2 ml; approx. 12 mM). The solution was cooled to 0° C. and dicyclohexylcarbodiimide (1.236 g; 6 mM) was added. The reaction mixture was stirred at 0° C. for 30 minutes and room temperature for 16 hours. The solution was then filtered and the filtrate evaporated at reduced pressure. The residue was then dissolved in ethyl acetate, washed with sodium bicarbonate solution and saturated sodium chloride solution and dried over anhydrous magnesium sulphate. Removal of the solvent afforded the crude thiol ester as a yellow oil. This oil was purified by column chromatography over silica gell (Type 60; 30 g). Elution with 5% methanol/chloroform afforded the pure prop-2-ene-thiol ester of monic acid A as a colourless oil (1.16 g; 49%).

BIOLOGICAL DATA (a) Human Bacteria

Table 1 shows the MIC values ($\mu$g/ml) of the compounds of Examples 1 to 8 against a number of human pathogens obtained by serial dilution in nutrient agar containing 5% 'chocolated' horse blood.

TABLE 1

| Organism | Compound of Example No: | | | | | | | |
|---|---|---|---|---|---|---|---|---|
| | 1 | 2 | 3 | 4 | 5 | 6 | 7 | 8 |
| Pasteurella multocida 1633 | 100 | 1.0 | 5.0 | 2.5 | 0.2 | — | 2.5 | 0.5 |
| Haemophilus influenzae Q1 | 25 | 0.2 | 0.5 | 0.2 | 0.05 | 2.5 | 0.2 | <0.02 |
| Haemophilus influenzae Wy21 | 50 | 0.2 | 0.5 | 0.2 | 0.1 | 2.5 | 0.5 | 0.05 |
| Neisseria catarrhalis 1502 | 2.5 | 0.2 | — | — | — | 0.05 | — | <0.02 |
| Neisseria flavescens 8263 | — | — | 0.5 | 0.2 | — | — | 0.5 | — |
| Bacillus subtilis | — | 0.2 | 0.5 | 0.2 | — | 2.5 | 5.0 | 0.05 |
| Staph. aureus Oxford | 25 | 0.2 | 0.5 | 0.2 | 0.1 | 2.5 | 10 | 0.05 |
| Staph. aureus Russell | — | 0.2 | 1.0 | 0.5 | 0.2 | 5.0 | 50 | 0.2 |
| Strep. pyrogenes A 64/848 | 100 | 0.5 | 0.2 | 0.1 | 2.5 | 10 | 5.0 | 0.5 |
| Strep. pyrogenes B 2788 | 100 | 1.0 | 2.5 | 1.0 | 0.5 | 5.0 | 5.0 | 0.5 |
| Strep. pyrogenes C 2761 | 100 | 1.0 | 1.0 | 0.5 | — | 10 | 5.0 | 0.5 |
| Strep. pneumoniae CN 33 | 2.5 | 2.5 | 0.2 | 0.2 | — | 2.5 | 2.5 | 0.2 |

(b) Veterinary Bacteria

Table 2 shows the MIC values (μg/ml) of some of the compounds of the Examples against a number of organisms important in veterinary infections.

TABLE 2

| Organism | Compound of Example No: | | | | | |
|---|---|---|---|---|---|---|
| | 2 | 3 | 5 | 6 | 7 | 8 |
| Bord. brontiseptica BO9 | 5 | 5 | 5 | 20 | 20 | 5 |
| Past. multocida PA1 | 0.625 | 2.5 | 0.625 | 2.5 | 1.25 | 1.25 |
| Past. haemolytica PA5 | 5 | 20 | 5.0 | 10 | 40 | 5 |
| Staph. aureus B4 | 0.312 | 1.25 | 0.312 | 2.5 | 40 | 0.312 |
| Staph. aureus 152 | 20 | 80 | 0.312 | — | 80 | 40 |
| Strep. uberis SPU1 | 0.312 | 0.156 | 0.625 | 1.25 | 0.625 | 0.516 |
| Strep. dysgalactiae SPD1 | 0.625 | 0.312 | 5.0 | 5 | 2.5 | 0.625 |
| Strep. agalactiae SPA1 | 0.625 | 1.25 | 5.0 | 5 | 5 | 0.625 |

(c) Anti-mycoplasma Activity

Table 3 shows the MIC values (μg/ml) of the compounds of Examples 1 to 8 against some important human and veterinary mycoplasma pathogens.

TABLE 3

| Organism | Compound of Example No: | | | | | | | |
|---|---|---|---|---|---|---|---|---|
| | 1 | 2 | 3 | 4 | 5 | 6 | 7 | 8 |
| (a) Determined in Friis' broth using the microtiter method | | | | | | | | |
| M. suipneumoniae Str. 11 | — | — | — | — | 0.156 | — | 0.625 0.156 | |
| M. suipneumoniae J2206/183 b | 15.6 | <0.5 | <0.5 | <0.5 | 0.156 | 15.6 | 2.5 | 1.25 |
| M. dispar H225 | — | — | — | — | <0.02 | — | 0.625 | 0.039 |
| M. dispar NCTC 10125 | <0.5 | <0.5 | <0.5 | <0.5 | <0.02 | <0.5 | 0.312 | <0.02 |
| M pneumoniae 427 a | >250 | 1.9 | 31.25 | 3.9 | 10 | >250 | 5.0 | 10 |
| M. pneumoniae ATCC 15492 | — | — | — | — | 5.0 | — | 2.5 | 5.0 |
| M. fermantans MWKL4 | 15.6 | <0.5 | 3.9 | <0.5 | <0.02 | 15.6 | <0.02 | <0.02 |
| M. pulmonis JB | 15.6 | <0.5 | <0.5 | <0.5 | <0.02 | 15.6 | <0.02 | <0.02 |
| (b) Determined by serial dilution in Friis agar | | | | | | | | |
| M. bovis ATCC 25025 | 15.6 | <0.5 | 62.5 | 3.9 | <0.02 | 15.6 | 0.039 | 0.078 |
| M. bovis NCTC 10131 | — | — | — | — | <0.02 | — | 0.039 | 0.039 |

We claim:

1. A compound of formula:

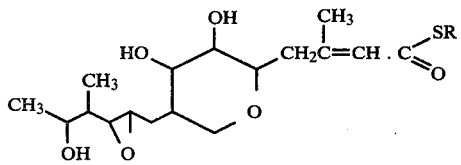

wherein R is a pharmaceutically acceptable ester-forming radical.

2. A compound according to claim 1 wherein R is alkyl of 1 to 20 carbon atoms or alkenyl of 2 to 8 carbon atoms, said alkyl or alkenyl being unsubstituted or substituted with phenyl or alkanoylamino of 1 to 6 carbon atoms; phenyl or $$-(CH_2)_n CO_2 R^1$$

wherein n is an integer from 1 to 20 and $R^1$ is hydrogen, a pharmaceutically acceptable salt-forming ion or alkyl of 1 to 6 carbon atoms.

3. A compound according to claim 2 wherein R is alkyl of 1 to 6 carbon atoms or alkenyl of 1 to 6 carbon atoms.

4. Methanethiol ester of monic acid A.

5. Ethanethiol ester of monic acid A.

6. n-Butanethiol ester of monic acid A.

7. Prop-2-enethiol ester of monic acid A.

8. A pharmaceutical or veterinary composition which comprises an antibacterially or antimycoplasmally effective amount of a compound according to claim 1 in combination with a pharmaceutical or veterinary carrier or excipient.

9. The method for the treatment of human and veterinary bacterial and mycoplasmal infections which comprises administering to a human or veterinary animal an antibacterially or antimycoplasmally effective amount of a compound according to claim 1.

* * * * *

UNITED STATES PATENT AND TRADEMARK OFFICE
CERTIFICATE OF CORRECTION

PATENT NO. : 4,216,223
DATED : August 5, 1980
INVENTOR(S) : JOHN PETER CLAYTON et al.

It is certified that error appears in the above-identified patent and that said Letters Patent are hereby corrected as shown below:

In column 9, line 43, "phosphorochloride" should read "phosphorochloridate".

In column 12, line 52, claim 3, "alkenyl of 1 to 6 carbon" should read "alkenyl of 2 to 6 carbon".

Signed and Sealed this

Tenth Day of February 1981

[SEAL]

Attest:

RENE D. TEGTMEYER

Attesting Officer

Acting Commissioner of Patents and Trademarks